(12) United States Patent
Suzuki et al.

(10) Patent No.: US 11,692,958 B2
(45) Date of Patent: Jul. 4, 2023

(54) GAS SENSOR DEVICE

(71) Applicant: Panasonic Intellectual Property Management Co., Ltd., Osaka (JP)

(72) Inventors: Shinya Suzuki, Kyoto (JP); Kiyokazu Itoi, Osaka (JP); Daisuke Suetsugu, Osaka (JP); Norimichi Noguchi, Osaka (JP); Nobutoshi Takagi, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 99 days.

(21) Appl. No.: 17/354,925

(22) Filed: Jun. 22, 2021

(65) Prior Publication Data

US 2022/0003706 A1 Jan. 6, 2022

(30) Foreign Application Priority Data

Jul. 2, 2020 (JP) .................................. 2020-114790

(51) Int. Cl.
*G01N 27/12* (2006.01)
*G01N 33/00* (2006.01)

(52) U.S. Cl.
CPC ......... *G01N 27/125* (2013.01); *G01N 33/005* (2013.01)

(58) Field of Classification Search
CPC .......................... G01N 27/125; G01N 33/005
See application file for complete search history.

(56) References Cited

U.S. PATENT DOCUMENTS

| 6,246,105 B1 * | 6/2001 | Morozumi ........ H01L 21/02164 |
| | | 257/E21.585 |
| 10,281,420 B2 * | 5/2019 | Muraoka ............. G01N 27/125 |

(Continued)

FOREIGN PATENT DOCUMENTS

| JP | 2000298108 A | * 10/2000 |
| JP | 2005-012016 | 1/2005 |

(Continued)

OTHER PUBLICATIONS

JP-2011043410-A-English (Year: 2011).*
JP-2011061005-A-translation (Year: 2011).*
JP-2000298108-A-translation (Year: 2000).*

*Primary Examiner* — Daniel S Larkin
*Assistant Examiner* — Fatemeh Esfandiari Nia
(74) *Attorney, Agent, or Firm* — Wenderoth, Lind & Ponack, L.L.P.

(57) ABSTRACT

A gas sensor device includes: a first electrode; a second electrode; a metal oxide layer that is disposed between the first electrode and the second electrode and is in contact with the first electrode and the second electrode; an interlayer insulating film that covers a part of the first electrode, a part of the second electrode, and a part of the metal oxide layer; and a hydrogen permeable film that allows only hydrogen to permeate, a local region that is in contact with the second electrode is provided inside the metal oxide layer, the local region having a higher oxygen deficiency than an oxygen deficiency of the other region in the metal oxide layer, an opening that exposes a gas contact portion which is a part of a main surface of the second electrode is provided in the interlayer insulating film, and the hydrogen permeable film is provided to cover at least the gas contact portion.

6 Claims, 1 Drawing Sheet

(56) References Cited

U.S. PATENT DOCUMENTS

| | | | | |
|---|---|---|---|---|
| 2003/0087513 A1* | 5/2003 | Noguchi | ........... | H01L 21/02074 |
| | | | | 438/624 |
| 2005/0258051 A1* | 11/2005 | Ono | ................... | G01N 27/125 |
| | | | | 204/431 |
| 2011/0049718 A1* | 3/2011 | Matsumoto | ....... | H01L 21/76844 |
| | | | | 257/E21.584 |
| 2015/0048361 A1* | 2/2015 | Yamakita | ............ | H01L 27/1225 |
| | | | | 257/43 |
| 2017/0131227 A1 | 5/2017 | Homma et al. | | |
| 2017/0269043 A1 | 9/2017 | Homma et al. | | |
| 2019/0219552 A1* | 7/2019 | Ikehashi | ............ | G01N 33/0036 |
| 2020/0173957 A1* | 6/2020 | Mouri | ................ | G01N 27/4072 |

FOREIGN PATENT DOCUMENTS

| | | | |
|---|---|---|---|
| JP | 2007-333625 | | 12/2007 |
| JP | 2011043410 A | * | 3/2011 |
| JP | 2011061005 A | * | 3/2011 |
| JP | 6145762 B | | 6/2017 |
| JP | 2017-173307 | | 9/2017 |

\* cited by examiner

GAS SENSOR DEVICE

BACKGROUND

1. Technical Field

The present disclosure relates to a gas sensor device.

2. Description of the Related Art

In order to realize a hydrogen society, it is necessary to secure safety and security for proceeding with improvement in infrastructure such as hydrogen storage and transport, and there has been an increasing importance of gas sensor devices. The gas sensor devices are required to be able to be used for a long period of time without being affected by electrode degradation due to water in any environments, particularly, in high-humidity environments. Also, when hydrogen-type fuel cells are distributed, or supply pipelines are constructed, and operations of hydrogen supply systems are started, it is necessary to secure security preservation in a case in which hydrogen leaks from conduits. Hydrogen sensors are required to have maintenance-free, power saving, environmentally resistant performance as important infrastructure equipment.

Here, an outline of a gas sensor device in Japanese Patent No. 6145762 will be described using FIG. 2. FIG. 2 is a sectional view illustrating an example of the gas sensor device described in Japanese Patent No. 6145762. As illustrated in FIG. 2, the gas sensor device in Japanese Patent No. 6145762 includes interlayer insulating film 107 that covers a laminated object in which substrate 101, insulating film 102, and first electrode 103, gas-sensitive resistance film 104, and second electrode 106 are laminated. Interlayer insulating film 107 is provided with opening 107a that is caused to detect target gas. A transition metal oxide is used as gas-sensitive resistance film 104, and the transition metal oxide (metal film) is pinched with first electrode 103 and second electrode 106. Gas-sensitive resistance film 104 is provided with local region 105 that is in contact with second electrode 106 and that is not in contact with first electrode 103.

According to the gas sensor device in Japanese Patent No. 6145762 with the configuration as described above, a current flowing between first electrode 103 and second electrode 106 concentrates on local region 105 including a metal oxide with high oxygen deficiency, and the temperature of local region 105 is thus raised. A portion of second electrode 106 that is in contact with local region 105 is heated due to heat generation at local region 105, and efficiency of hydrogen atoms dissociating from hydrogen-containing gas is enhanced. As a result, if the hydrogen-containing gas is present in the gas that is a target to be inspected, then the hydrogen atoms dissociated from the hydrogen-containing gas at second electrode 106 are bonded to oxygen atoms inside local region 105, and a resistance value of local region 105 decreases. It is possible to detect the hydrogen-containing gas included in the gas based on a decrease in resistance value between first electrode 103 and second electrode 106 achieved through contact of the gas that is a target to be inspected with second electrode 106, using such a change in resistance value. The gas sensor device in Japanese Patent No. 6145762 can detect the hydrogen-containing gas without heating using a heater and thus has excellent power saving properties.

SUMMARY

A gas sensor device according to an aspect of the present disclosure includes: a first electrode; a second electrode; a metal oxide layer that is disposed between the first electrode and the second electrode and is in contact with the first electrode and the second electrode; an interlayer insulating film that covers a part of the first electrode, a part of the second electrode, and a part of the metal oxide layer; and a hydrogen permeable film that allows only hydrogen to be permeate, a local region that is in contact with the second electrode is provided inside the metal oxide layer, the local region having a higher oxygen deficiency than an oxygen deficiency of the other region in the metal oxide layer, an opening that exposes a gas contact portion which is a part of a main surface of the second electrode is provided in the interlayer insulating film, and the hydrogen permeable film is provided to cover at least the gas contact portion.

DETAILED DESCRIPTION

Since opening 107a for bringing the target gas into contact with second electrode 106 is provided in interlayer insulating film 107 in the gas sensor device described in Japanese Patent No. 6145762, there is a concern that second electrode 106 is covered with moisture in a high-humidity environment and a gas detection ability is degraded.

The present disclosure provides a gas sensor device capable of improving moisture-resistant performance in a high-humidity environment.

Figure 1:
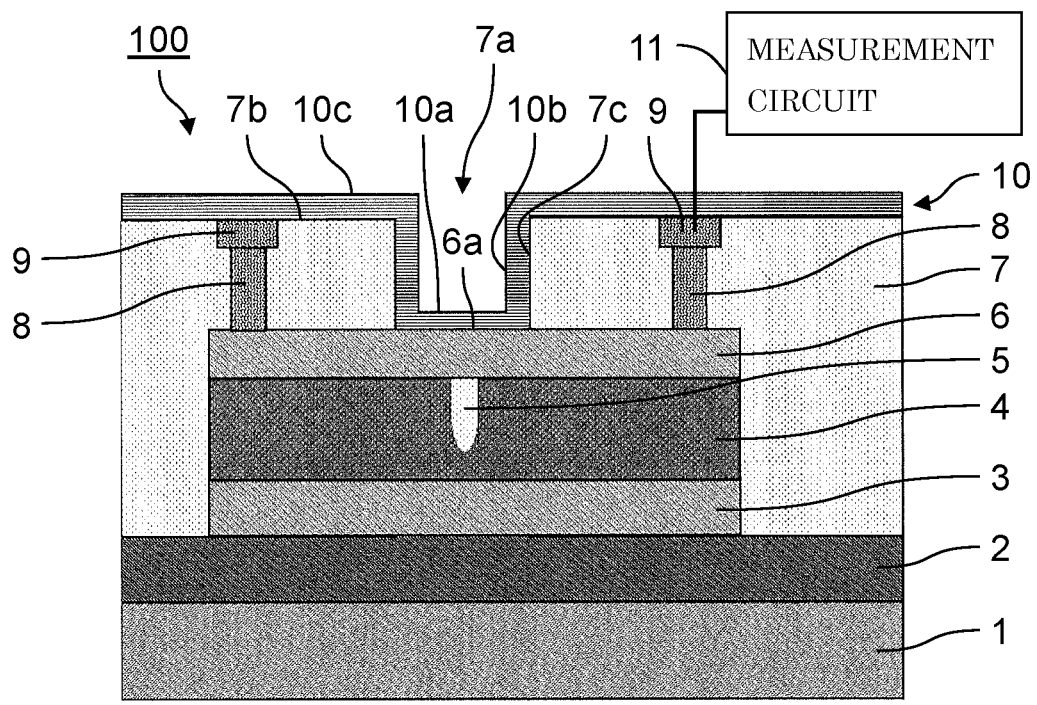
FIG. 1 is a sectional view of a gas sensor device according to an exemplary embodiment of the present disclosure.
Figure 2:
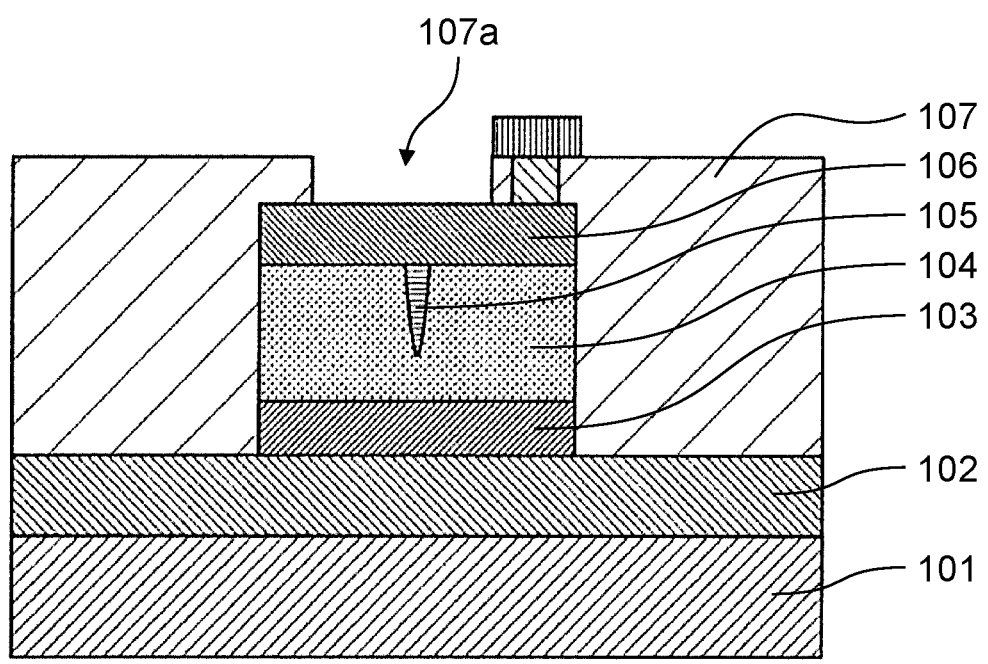
FIG. 2 is a sectional view of a gas sensor device described in Japanese Patent No. 6145762.

Hereinafter, an exemplary embodiment of the present disclosure will be described with reference to the drawings. The drawings are schematic or conceptual drawings, and elements representing the same configurations, operations, and effects are not necessarily the same as the real elements. Even in a case in which the drawings represent the same parts, there may also be a case in which dimensions and ratios are differently expressed depending on drawings. FIG. 1 is a sectional view illustrating a configuration example of a gas sensor according to an exemplary embodiment of the present disclosure.

Structure of Gas Sensor Device

As illustrated in FIG. 1, gas sensor device 100 includes substrate 1, insulating film 2 disposed on substrate 1, first electrode 3 disposed above insulating film 2, second electrode 6, gas-sensitive resistance film 4 that is pinched between first electrode 3 and second electrode 6, interlayer insulating film 7, via 8, wiring conductor 9, and hydrogen permeable film 10.

Substrate 1 has a first main surface that is an upper surface. Although it is possible to use, as substrate 1, a silicon single-crystal substrate, a semiconductor substrate, a resin material, or the like, substrate 1 is not limited to these materials.

Insulating film 2 has a first main surface that is a lower surface and a second main surface that is an upper surface. Insulating film 2 can be molded by a thermal oxidation method in a case in which silicon is used as a material. For example, it is possible to form insulating film 2 of silicon dioxide by oxidizing silicon in oxygen and water vapor in a high temperature atmosphere. The thickness of molded insulating film 2 may be any thickness having an insulating function and is, for example, equal to or greater than 100 nm and equal to or less than 1000 nm.

First electrode 3 has a first main surface that is a lower surface and a second main surface that is an upper surface. Second electrode 6 has a third main surface that is a lower surface and a fourth main surface that is an upper surface. The second main surface of first electrode 3 and the third main surface of second electrode 6 are disposed to face each other. Gas-sensitive resistance film 4 is disposed to be in contact with the second main surface of first electrode 3 and the third main surface of second electrode 6.

The materials of first electrode 3 and second electrode 6 are selected from, for example, Pt (platinum), Ir (iridium), Pd (palladium), Ag (silver), Ni (nickel), W (tungsten), Cu (copper), Al (aluminum), Ta (tantalum), Ti (titanium), TiN (titanium nitride), TaN (tantalum nitride), and TiAlN (titanium aluminum nitride). Specifically, a material that has a catalytic action of dissociating hydrogen atoms from gas molecules including the hydrogen atoms, such as platinum (Pt), iridium (Ir), or palladium (Pd), is used as a material for second electrode 6. Also, a material with a lower standard electrode potential as compared with metal constituting a metal oxide, such as tungsten (W), nickel (Ni), tantalum (Ta), titanium (Ti), aluminum (Al), tantalum nitride (TaN), or titanium nitride (TiN), for example, may be used as a material for first electrode 3. A larger value of the standard electrode potential represents a property that the material is less likely to be oxidized.

As a method of molding these first electrode 3 and second electrode 6, it is possible to use a dry process based on a sputtering method. For example, molding of first electrode 3 based on the sputtering method is performed by installing a metal film, which is a target, and insulating film 2 in vacuum such that the metal film and insulating film 2 face each other, applying a voltage thereto to ionize inert gas such as nitrogen or argon, causes the ionized inert gas to collide against the target surface, and causing components repelled from the target to be deposited and laminated on insulating film 2. At this time, the thickness of the metal layer that is caused to be deposited and laminated is preferably equal to or greater than 50 nm and equal to or less than 300 nm. The reason is because gas sensitivity becomes the highest. Second electrode 6 can be molded by causing components repelled from the target to be deposited and laminated on gas-sensitive resistance film 4 using a sputtering method similar to that for first electrode 3.

Gas-sensitive resistance film 4 is disposed between first electrode 3 and second electrode 6. Gas-sensitive resistance film 4 is a layer with a resistance value that reversibly changes based on an electrical signal given between first electrode 3 and second electrode 6. As gas-sensitive resistance film 4, a metal oxide with a resistance value that changes in accordance with a voltage given between first electrode 3 and second electrode 6 and presence/absence of hydrogen-containing gas in the gas with which second electrode 6 is brought into contact is used.

Gas-sensitive resistance film 4 is an example of a metal oxide layer containing an oxygen-deficient metal oxide. The oxygen-deficient metal oxide is an indefinite ratio compound and means a metal oxide lacking oxygen, such as zinc oxide (ZnO), cadmium oxide, titanium oxide, or aluminum oxide ($Al_2O_3$). A base metal of the metal oxide may be at least one selected from a group consisting of transition metals such as tantalum (Ta), hafnium (Hf), titanium (Ti), zirconium (Zr), niobium (Nb), tungsten (W), nickel (Ni), and iron (Fe), and aluminum (Al). In a case in which a hafnium oxide is used as the metal oxide contained by gas-sensitive resistance film 4, and x is equal to or greater than 1.6 when the composition thereof is expressed as $HfO_x$, it is possible to cause the resistance value of gas-sensitive resistance film 4 to be stably changed. In this case, the film thickness of the hafnium oxide may be equal to or greater than 3 nm and equal to or less than 4 nm. In a case in which a zirconium oxide is used as the metal oxide contained by gas-sensitive resistance film 4, and x is equal to or greater than 1.4 when the composition thereof is expressed as $ZrO_x$, it is possible to cause the resistance value of gas-sensitive resistance film 4 to be stably changed. In this case, the film thickness of the zirconium oxide may be equal to or greater than 1 nm and equal to or less than 5 nm. In a case in which a tantalum oxide is used as the metal oxide contained by gas-sensitive resistance film 104, and x is equal to or greater than 2.1 when the composition thereof is expressed as $TaO_x$, it is possible to cause the resistance value of gas-sensitive resistance film 4 to be stably changed. Gas-sensitive resistance film 4 may be molded using the dry process based on the sputtering method.

Local region 5 is provided inside gas-sensitive resistance film 4. Local region 5 has higher oxygen deficiency than the other region (the region that is different from local region 5) in gas-sensitive resistance film 4. Local region 5 is formed inside gas-sensitive resistance film 4 by applying a voltage between first electrode 3 and second electrode 6. Local region 5 that is in contact with second electrode 6 and that is not in contact with first electrode 3 is formed inside gas-sensitive resistance film 4 as illustrated in FIG. 1 through an application of an initial break voltage. Here, the initial break voltage may be a voltage with a larger absolute value than an ordinary writing voltage to be applied between first electrode 3 and second electrode 6, in order to reversibly transition gas-sensitive resistance film 4 between a high resistance state and a low resistance state. The initial break voltage may be a voltage with an absolute value that is smaller than that of the writing voltage. In this case, the initial break voltage may be repeatedly applied or may be successively applied for a predetermined time.

The oxygen deficiency of the metal oxide contained in local region 5 reversibly changes in accordance with an application of an electrical signal given between first electrode 3 and second electrode 6 and presence/absence of hydrogen-containing gas in the gas with which second electrode 6 is brought into contact. If the oxygen deficiency of the metal oxide contained in local region 5 increases, then the resistance value of local region 5 decreases. If hydrogen gas is present in the gas that is a target to be inspected, then the hydrogen atoms dissociated from the hydrogen gas in second electrode 6 bond to oxygen atoms in local region 5, the resistance value of local region 5 decreases, and the resistance value of gas-sensitive resistance film 4 thus decreases. Due to such a property, it is possible to detect the hydrogen gas contained in the gas based on a decrease in resistance value between first electrode 3 and second electrode 6 achieved through contact of the gas that is a target to be inspected with second electrode 6.

If local region 5 is present in gas-sensitive resistance film 4, a current in gas-sensitive resistance film 4 flows intensively in local region 5 when an electrical signal is applied between first electrode 3 and second electrode 6. Local region 5 is small. Therefore, a relatively large temperature rise occurs due to heat generation caused by a current of about several tens of µA (that is, power consumption of less than 0.1 mW) when a voltage of about 1 V is applied to read the resistance value, for example. Therefore, it is possible to enhance efficiency of dissociation of hydrogen atoms from the hydrogen-containing gas by configuring second electrode 6 with a metal with a catalytic action, for example, Pt and heating the portion of second electrode 6, which is in contact with local region 5, through heat generation at local region 5. In other words, it is possible to detect the hydrogen gas even of the concentration of the hydrogen gas contained in the gas that is a target to be inspected is low.

Interlayer insulating film 7 is provided to cover insulating film 2, first electrode 3, second electrode 6, and gas-sensitive resistance film 4 and not to cover gas contact portion 6a, which is a portion of the fourth main surface of second electrode 6. In other words, interlayer insulating film 7 has opening 7a for causing gas contact portion 6a of second electrode 6 to be exposed to outside and bringing second electrode 6 into contact with the gas that is a target to be inspected. Interlayer insulating film 7 can be configured with a non-conductor insulating material such as a silicon dioxide or a glass film, for example, and can be molded by a spin coating method or the like. The thickness of interlayer insulating film 7 is preferably equal to or greater than 0.1 μm and equal to or less than 300 μm. In a case in which the non-conductor insulating material constituting interlayer insulating film 7 has sufficient insulating performance, the thickness of interlayer insulating film 7 may not fall within the aforementioned range. Gas contact portion 6a is a portion of second electrode 6 that is brought into contact with hydrogen permeable film 10. In other words, gas contact portion 6a is a portion of second electrode 6.

Via 8 is disposed at a portion of interlayer insulating film 7 that covers second electrode 6. Via 8 penetrates through interlayer insulating film 7 and is connected to second electrode 6. Wiring conductor 9 is disposed on via 8. Wiring conductor 9 is connected to measurement circuit 11 and an arithmetic operation circuit. If the hydrogen-containing gas comes into contact with gas contact portion 6a of second electrode 6, then the resistance value of gas-sensitive resistance film 4 decreases, and the value of the current flowing through gas-sensitive resistance film 4 changes with the decrease in resistance value. Such a change in current value can be measured by measurement circuit 11. It is possible to calculate the concentration of the hydrogen gas with the arithmetic operation circuit based on the measurement result of measurement circuit 11.

Interlayer insulating film 7 is provided with hydrogen permeable film 10 disposed to cover upper surface 7b of interlayer insulating film 7, side wall 7c that defines opening 7a, and gas contact portion 6a of second electrode 6. Hydrogen permeable film 10 includes first covering portion 10a that covers gas contact portion 6a of second electrode 6, second covering portion 10b that covers side wall 7c, and third covering portion 10c that covers upper surface 7b of interlayer insulating film 7. It is only necessary for hydrogen permeable film 10 to have at least first covering portion 10a.

Hydrogen permeable film 10 is made of a porous film or a non-porous film. Since hydrogen permeable film 10 can be used in gas or a solution as a microfiltration membrane, hydrogen permeable film 10 can be used as a moisture-proof film against water by focusing on the filtration performance. In a case in which hydrogen gas comes into contact with densely molded hydrogen permeable film 10, it is possible to detect the hydrogen gas by only hydrogen being atomically dissociated, dissolved, diffused, and recombined and reaching second electrode 6. Although it is possible to apply a metal thin film of Pd or a Pd alloy, a Pd—Cu alloy, TiN, or the like to hydrogen permeable film 10, the material of the hydrogen permeable film is not limited thereto. As a method of forming hydrogen permeable film 10, there is a sputtering method. In a case in which hydrogen permeable film 10 is formed by the sputtering method, for example, it is necessary to set the film thickness of hydrogen permeable film 10 to be equal to or greater than 10 nm and equal to or less than 100 nm in order to cause gas sensor device 100 to have sufficient detection performance. The film thickness of hydrogen permeable film 10 is more preferably equal to or less than 50 nm.

Manufacturing Method of Gas Sensor Device

Next, an example of a manufacturing method of gas sensor device 100 will be described.

Insulating film 2 with a thickness of 200 nm is formed on substrate 1, which is single crystal silicon, by a thermal oxidation method. A Pt film with a thickness of 100 nm, for example, is formed as first electrode 3 on insulating film 2 by the sputtering method. It is also possible to form an adhesion layer of Ti, TiN, or the like between first electrode 3 and insulating film 2 by the sputtering method.

Thereafter, an oxygen-deficient metal oxide layer that serves as gas-sensitive resistance film 4 is formed on first electrode 3 by a reactive sputtering method using a Ta target, for example. As described above, gas-sensitive resistance film 4 configured with a metal oxide of TaO is formed. In regard to the thickness of gas-sensitive resistance film 4, there is a disadvantage that the initial resistance value becomes excessively high if the thickness is too thick, and there is also a disadvantage that a stable resistance change cannot be obtained if the thickness is too thin. For the above reasons, the thickness of gas-sensitive resistance film 4 may be equal to or greater than about 1 nm and equal to or less than about 8 nm.

Next, a Pt film with a thickness of 150 nm, for example, is formed as second electrode 6 on gas-sensitive resistance film 4 by the sputtering method. Next, a photolithography process is performed for formation using a photoresist. Thereafter, first electrode 3, gas-sensitive resistance film 4, and second electrode 6 are formed into element shapes through dry etching. Thereafter, interlayer insulating film 7 is formed to cover insulating film 2, first electrode 3, gas-sensitive resistance film 4, and second electrode 6 in a spin coating process.

A via hole that reaches a part of the upper surface of second electrode 6 is formed in interlayer insulating film 7 by a dry etching method. Next, a conductor film is formed to fill the upper surface of interlayer insulating film 7 and the inside of the via hole. Thereafter, the conductor film on interlayer insulating film 7 is removed to form via 8 in the via hole. Moreover, wiring conductor 9 that is connected to via 8 is formed by disposing a new conductor film on interlayer insulating film 7 and performing patterning thereon.

Next, opening 7a from which a part of the upper surface of second electrode 6 is exposed is formed in interlayer insulating film 7 through etching. Thereafter, local region 5 is formed inside gas-sensitive resistance film 4 by applying a voltage between first electrode 3 and second electrode 6.

Next, a Pd film with a thickness of 100 nm is formed as hydrogen permeable film 10 on second electrode 6 and interlayer insulating film 7 exposed from opening 7a by the sputtering method. At this time, in a case in which the sputtering incident angle at the time of film formation with respect to upper surface 7b of interlayer insulating film 7 (an angle at which the film forming material is incident from a direction that perpendicularly intersects upper surface 7b) is changed from 0° to 45°, hydrogen permeable film 10 formed by the sputtering method has a structure in which a difference occurs between film thicknesses of first covering portion 10a that covers gas contact portion 6a of second electrode 6 and second covering portion 10b that covers side wall 7c that defines opening 7a. At this time, there is a concern that if second covering portion 10b is excessively thin, it is not possible to secure the moisture-proof performance of interlayer insulating film 7 provided with a wiring pattern, which is not illustrated. Also, in a case in which first covering portion 10a is formed to have a thickness of equal to or greater than 100 nm, a disadvantage may occur in hydrogen sensitivity. Therefore, it is preferable that second covering portion 10b be thick and first covering portion 10a be thin. In a case in which the thickness of second covering portion 10b is equal to or greater than 50 nm and equal to or less than 100 nm, for example, the thickness of first covering portion 10a is preferably equal to or greater than 10 nm and equal to or less than 30 nm. In a case in which it is desired to form first covering portion 10a to be yet thinner, it is only necessary to set the sputtering incident angle at the time of film formation with respect to upper surface 7b of interlayer insulating film 7 to be yet larger. It is thus possible to manufacture gas sensor device 100 with faster gas responsiveness. Gas sensor device 100 is completed through the processes described above.

Actions and Effects of Gas Sensor Device

According to the gas sensor device of the present disclosure, it is possible to improve moisture-resistant performance in a high-humidity environment. Specifically, according to gas sensor device 100 as described above, gas contact portion 6a is covered with hydrogen permeable film 10, and it is thus possible to bring only hydrogen that is a target to be inspected into contact while preventing moisture from coming into contact with gas contact portion 6a. Therefore, it is possible to improve the moisture-resistant performance of gas sensor device 100 in a high-humidity environment. Since first covering portion 10a is formed to be thinner than second covering portion 10b, in particular, it is possible to provide gas sensor device 100 capable of securing the moisture-proof performance of interlayer insulating film 7 and having faster gas responsiveness.

The gas sensor device according to the present disclosure is useful as a gas sensor with excellent power saving and environmentally resistant performance.

What is claimed is:

1. A gas sensor device comprising:
   a first electrode;
   a second electrode;
   a metal oxide layer that is disposed between the first electrode and the second electrode and is in contact with the first electrode and the second electrode;
   an interlayer insulating film that covers a part of the first electrode, a part of the second electrode, and a part of the metal oxide layer; and
   a hydrogen permeable film that allows only hydrogen to permeate,
   wherein a local region that is in contact with the second electrode is provided inside the metal oxide layer, the local region having a higher oxygen deficiency than an oxygen deficiency of the other region in the metal oxide layer,
   an opening that exposes a gas contact portion which is a part of a main surface of the second electrode is provided in the interlayer insulating film, and
   the hydrogen permeable film includes a first covering portion that covers the gas contact portion at a bottom of the opening and a second covering portion that covers side walls that defines the opening, wherein a thickness of the first covering portion is less than a thickness of the second covering portion.

2. The gas sensor device of claim 1, wherein the hydrogen permeable film includes at least one selected from Pd, a Pd alloy, a Pd—Cu alloy, and TiN.

3. The gas sensor device of claim 1, further comprising:
   a measurement circuit that measures a change in value of a current flowing through the metal oxide layer due to contact of hydrogen-containing gas with the gas contact portion of the second electrode.

4. The gas sensor device of claim 1, wherein:
   the thickness of the first covering portion is equal to or greater than 10 nm and equal to or less than 30 nm, and
   the thickness of the second covering portion is equal to or greater than 50 nm and equal to or less than 100 nm.

5. A gas sensor device comprising:
   a first electrode;
   a second electrode;
   a metal oxide layer that is disposed between the first electrode and the second electrode and is in contact with the first electrode and the second electrode;
   an interlayer insulating film that covers a part of the first electrode, a part of the second electrode, and a part of the metal oxide layer; and
   a hydrogen permeable film that allows only hydrogen to permeate,
   wherein a local region that is in contact with the second electrode is provided inside the metal oxide layer, the local region having higher oxygen deficiency than the other region in the metal oxide layer,
   an opening that exposes a gas contact portion which is a part of a main surface of the second electrode is provided in the interlayer insulating film,
   the hydrogen permeable film is provided to cover at least the gas contact portion,
   the hydrogen permeable film includes a first covering portion that covers the gas contact portion at a bottom of the opening and a second covering portion that covers side walls that define the opening, wherein a thickness of the first covering portion is less than a thickness of the second covering portion,
   the first covering portion is formed to be thinner than the second covering portion,
   the hydrogen permeable film includes at least one selected from Pd, a Pd alloy, a Pd—Cu alloy, and TiN, and
   the gas sensor device further comprises a measurement circuit that measures a change in value of a current flowing through the metal oxide layer due to contact of hydrogen-containing gas with the gas contact portion of the second electrode.

6. The gas sensor device of claim 5, wherein:
   the thickness of the first covering portion is equal to or greater than 10 nm and equal to or less than 30 nm, and
   the thickness of the second covering portion is equal to or greater than 50 nm and equal to or less than 100 nm.

* * * * *